United States Patent
Wu

(10) Patent No.: US 11,771,654 B2
(45) Date of Patent: *Oct. 3, 2023

(54) MICROPARTICLES AND NANOPARTICLES HAVING NEGATIVE SURFACE CHARGES

(71) Applicant: CYTODIGM, INC., Natick, MA (US)

(72) Inventor: Bin Wu, Lexington, MA (US)

(73) Assignee: Cytodigm, Inc., Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/879,316

(22) Filed: Aug. 2, 2022

(65) Prior Publication Data

US 2022/0387319 A1   Dec. 8, 2022

Related U.S. Application Data

(63) Continuation of application No. 14/916,439, filed as application No. PCT/US2013/073019 on Dec. 4, 2013, now Pat. No. 11,439,594.

(60) Provisional application No. 61/733,216, filed on Dec. 4, 2012.

(51) Int. Cl.
| | |
|---|---|
| A61K 9/14 | (2006.01) |
| A61K 9/19 | (2006.01) |
| A61K 9/51 | (2006.01) |
| A61K 47/61 | (2017.01) |
| A61K 47/59 | (2017.01) |
| A61K 47/69 | (2017.01) |
| A61K 47/58 | (2017.01) |
| A61K 9/16 | (2006.01) |
| B82Y 5/00 | (2011.01) |

(52) U.S. Cl.
CPC ............ *A61K 9/146* (2013.01); *A61K 9/1635* (2013.01); *A61K 9/1647* (2013.01); *A61K 9/1652* (2013.01); *A61K 9/1682* (2013.01); *A61K 9/19* (2013.01); *A61K 9/5153* (2013.01); *A61K 9/5161* (2013.01); *A61K 9/5192* (2013.01); *A61K 47/58* (2017.08); *A61K 47/593* (2017.08); *A61K 47/61* (2017.08); *A61K 47/6931* (2017.08); *A61K 47/6933* (2017.08); *A61K 47/6937* (2017.08); *B82Y 5/00* (2013.01); *Y02A 50/30* (2018.01)

(58) Field of Classification Search
CPC .... A61K 9/146; A61K 9/1635; A61K 9/1682; A61K 9/5153
See application file for complete search history.

(56) References Cited

U.S. PATENT DOCUMENTS

| 7,993,678 B2 | 8/2011 | Toemmeraas et al. |
|---|---|---|
| 9,913,883 B2 | 3/2018 | Getts |
| 10,780,053 B2 | 9/2020 | Wu |
| 2004/0087528 A1 | 5/2004 | Levy et al. |
| 2004/0265392 A1 | 12/2004 | Tovar et al. |
| 2005/0053667 A1 | 3/2005 | Irvine et al. |
| 2005/0163853 A1* | 7/2005 | Szente ............... A61L 27/54 424/486 |
| 2008/0317795 A1 | 12/2008 | Traynor et al. |
| 2009/0136585 A1 | 5/2009 | Labhasetwar et al. |
| 2009/0305874 A1 | 12/2009 | Pfeifer et al. |
| 2010/0112073 A1 | 5/2010 | Sabliov et al. |
| 2011/0065807 A1 | 3/2011 | Radovic-moreno et al. |
| 2011/0293644 A1 | 12/2011 | Anderson et al. |
| 2012/0231069 A1 | 9/2012 | Nowotnik et al. |

FOREIGN PATENT DOCUMENTS

| EP | 0340628 A2 | 11/1989 |
|---|---|---|
| EP | 2070521 A1 | 6/2009 |
| RU | 2139900 A | 10/1999 |
| RU | 2257198 C1 | 8/2004 |
| WO | 8800211 A1 | 1/1988 |
| WO | 9316724 A1 | 9/1993 |
| WO | 9525751 A1 | 9/1995 |
| WO | 9635418 A1 | 11/1996 |
| WO | 9845335 A1 | 10/1998 |
| WO | 2005015160 A2 | 2/2005 |
| WO | 2009020865 A1 | 2/2009 |
| WO | 2010060155 A1 | 6/2010 |
| WO | 2010085509 A1 | 7/2010 |
| WO | 2012052565 A1 | 4/2012 |
| WO | 2012065153 A2 | 5/2012 |
| WO | 2013192532 A2 | 12/2013 |
| WO | 2014160465 A2 | 10/2014 |
| WO | 2015149820 A1 | 10/2015 |

OTHER PUBLICATIONS

Vandervoort et al, Biocompatible Stabilizers in the Preparation of PLGA Nanoparticles: A Factorial Design Study, International Journal of Pharmaceutics, vol. 238, pp. 77-92 (Year: 2002).*
Varges et al, Rheological Characterization of Carbopol Dispersions in Water and Water/Glycerol Solutions, Fluids, vol. 4, No. 3, pp. 1-20 (Year: 2019).*
Keegan, Biodegradable Microspheres with Enhanced Capacity for Covalently Bound Surface Ligands, Macromol, vol. 37, p. 9779-9784. (Year: 2004).*
Application Data Sheet for U.S. Appl. No. 61/887,112.

(Continued)

*Primary Examiner* — Carlos A Azpuru

(74) *Attorney, Agent, or Firm* — Elmore Patent Law Group, P.C.; Carolyn S. Elmore

(57) ABSTRACT

This invention provides methods for producing a polymer particle which contains unusually high negative charges on the surface of the particle. Preferably, the polymer is pharmaceutically acceptable. The negative charges can be conferred by chemical groups such as carboxyl, sulfonate, nitrate, fluorate, chloride, iodide, persulfate, and many others, with carboxyl group being preferred. The invention also provides polymer particle produced by the methods of the invention.

15 Claims, No Drawings

(56) References Cited

OTHER PUBLICATIONS

Inventor Assignments for U.S. Appl. Nos. 61/887,112, 61/865,389, 61/869,279; PCT Application Nos. US2013047079, US2014050962.
U.S. Appl. No. 61/779,182, filed Mar. 13, 2013.
U.S. Appl. No. 61/844,961, filed Jul. 11, 2013.
U.S. Appl. No. 61/865,389, filed Aug. 13, 2013.
U.S. Appl. No. 61/865,392, filed Aug. 13, 2013.
U.S. Appl. No. 61/887,212, filed Oct. 4, 2013.
Zetasizer Nano Series User Manual-Ch. 3 and 5, MAN0485 Issue 1.1, Apr. 2013. Malvern Instruments Ltd.
Abdelkader, H. et al., "Controlled and Continuous Release Ocular Drug Delivery Systems: Pros and Cons", Current Drug Delivery, vol. 9, No. 4, 2012, 1-10.
Akagi, T. et al., "Biodegradable Nanoparticles as Vaccine Adjuvants and Delivery Systems: Regulation of Immune Responses by Nanoparticle-Based Vaccine", Adv. Polym. Sci., vol. 247, Oct. 20, 2011, 31-64.
Anderson, R. et al., "T Cells in Peripheral Blood after Gluten Challenge in Coeliac Disease", Gut, vol. 54, doi: 10.1136/gut.2004.059998, Aug. 11, 2005, 1217-1223.
Bagratashvili, V. N. et al., "Getting Micro-Biorezorbiruemyh Polymers Using Supercritical Environments", Supercritical Fluids: Theory and Practice vol. 2(1), 2007, 53-60.
Batanero, E. et al., "Biodegradable Poly (DL-Lactide Glycolide) Microparticles as a Vehicle for Allergen-Specific Vaccines: A Study Performed with Ole e 1, the Main Allergen of Olive Pollen", J. Immunolog. Methods, vol. 259, 2002, 87-94.
Bibikova, O. A. et al., "New types of nanomaterials: Golden powder nanosfer, nanosterzhnej, nanozvezd and zolotoserebrjanyh nanocells", Russian Nanotechnology, vol. 7(11), Nov. 2012, 87-94.
Buyuktimkin, B. et al., "Vaccine-like controlled-release delivery of an immunomodulating peptide to treat experimental autoimmune encephalomyelitis", Mol. Pharmaceutics, 9(4), Feb. 29, 2012, 979-985.
Choi, J. et al., "Influence of the Degree of Ionization on Weak Polyelectrolyte Multilayer Assembly", Macromolecules, 38(1), 2005, 116-124.
Cohen-Sela, et al., "A new double emulsion solvent diffusion technique for encapsulating hydrophilic molecules in PLGA nanoparticles", J. Controlled Release, 133, 2009, 90-95.
Govender, T. et al., "PLGA nanoparticles prepared by nanoprecipitation: drug loading and release studies of a water soluble drug", J. Controlled Release, 57, 1999, 171-185.
Gritskova, I. A. et al., "Synthesis of Polymeric Microspheres Containing Inorganic Nanoparticles", MITHT Journal, 6(5), 2011, 9-20.
Hans, et al., "Biodegradable nanoparticles for drug delivery and targeting", Current Opinion in Solid State and Materials Science, vol. 6, 2002, 319-327.
Heslinga, Michael J. et al., "Fabrication of biodegradable spheroidal microparticles for drug delivery applications", J. Controlled Release, 138, 2009, 235-242.
Jain, "The manufacturing techniques of various drug loaded biodegradable poly(lactide-co-glycolide)(PLGA) devices", Biomaterials, 21, 2000, 2475-2490.
Khlebtsov, B. N. et al., "New types of nanomaterials: Powders of gold nanospheres, nanorods, nanonostars, and gold-silver nanocages", Nanotechnologies in Russia, vol. 8, Nos. 3-4, 2013, 209-219.
Lamprecht, et al., "Influences of process parameters on nanoparticle preparation performed by a double emulsion pressure homogenization technique", International Journal of Pharmaceutics, vol. 196, 2000, 177-182.
Lewis, Sr., R. Hawley's Condensed Chemical Dictionary, 15th Ed., 2007, 472, 1163.
Molyneux, P. et al., "Water-Soluble Synthetic Polymers: Properties and Behavior, vol. II", CRC Press, 1984, 1-16.
Nam, S-H. et al., "Curcumin-Loaded PLGA Nanoparticles Coating onto Metal Stent by Electrophoretic Deposition Techniques", Bulletin of the Korean Chem. Soc., 28(3), Mar. 20, 2007.
Rowe, R. et al., Handbook of Pharmaceutical Excipients, 6th ed., 2009, 110-114.
Sahoo, S. K. et al., "Residual polyvinyl alcohol associated with poly (D,L-lactide-co-glycolide) nanoparticles affects their physical properties and cellular uptake", J. Controlled Release, 82, 2002, 105-114.
Scholes, P. D. et al., "Detection and determination of surface levels of poloxamer and PVA surfactant on biodegradable nanospheres using SSIMS and XPS", J. Controlled Release, vol. 59, 1999, 261-278.
Song, et al., "PLGA nanoparticles simultaneously loaded with vincristine sulfate and verapamil hydrochloride: Systemic study of particle size and drug entrapment efficiency", Int. J. Pharma., 350, 2008, 320-329.
Stolnik, S. et al., "The colloidal properties of surfactant-free biodegradable nanospheres from poly(beta-malic acid-co-benzyl malate X )sand poly(lactic acid-co-glycolide)", Colloids and Surfaces A: Physicochemical and Engineering Aspects, vol. 97, 1995, 235-245.
Sussman, "Functionalized Polymeric Nanoparticles", Mat. Res. Soc. Symp., Proc., 818, 2004, M12.9.1-M12.9.6.
Tewes, F. et al., "Comparative study of doxorubicin-loaded poly(lactide-co-glycolide) nanoparticles prepared by single and double u emulsion methods", Euro. J. Pharma and Biopharma., 66, 2007, 488-492.
Vandervoort, J. et al., "Biocompatible stabilizers in the preparation of PLGA nanoparticles: a factorial design study", International Journal of Pharmaceutics, vol. 238, 2002, 77-92.
Varges, P. et al., "Rheological Characterization of Carbopol Dispersions in Water and in Water/Glycerol Solutions", Fluids, vol. 4, No. 3, 2019, 1-20.
Zou, W. et al., "New approach for local delivery of rapamycin by bioadhesive PLGA-carbopol nanoparticles", Drug Delivery, vol. 16, No. 1, 2009, 15-53.
Clinicaltrials.gov, Trial record for nexvax2, Aug. 23, 2018.
Cour/Takeda press release dated Oct. 22, 2019.
Declaration of Ciaran P. Kelly I filed Mar. 10, 2021 regarding Opposition to EP 3 033 102 of Northwestern University.
"Cour Pharmaceuticals Receives FDA Fast Track Designation for TIMP-GLIA—A Novel Treatment for Celiac Disease Under Clinical Development", Press Release, Cour Pharmaceuticals, Jan. 8, 2018, 1-2.
Press Release, Jun. 25, 2019, ImmusanT Discontinues Phase 2 Clinical Trial for Nexvax2 in Patients With Celiac Disease.
Search Results, ClinicalTrials.gov, dated Apr. 22, 2021.
U.S. Appl. No. 61/869,279, filed Aug. 23, 2013.
U.S. Appl. No. 61/887,112, filed Oct. 4, 2013.
"World's First Celiac Vaccine Gains FDA Fast-Track Designation During Phase 2 Trial", Nutrition Insight, web article, Jan. 3, 2019.
Declaration of Daniel R. Getts submitted as part of U.S. Appl. No. 14/624,463, filed Feb. 17, 2015, 1-10.
Declaration of Joseph R. Podojil filed Mar. 12, 2021 regarding Opposition to EP 3 033 102 of Northwestern University, 1-16.
European Patent Application 89107615.0 filed Apr. 27, 1989, 1-19.
PCT Request Form for PCT/US14/50962, filed Aug. 13, 2014, 1-5.
License agreement between Northwestern University and Cour Pharmaceutical Development, Inc., May 14, 2013, 1-15.
"Carboxylate-Surface-Functionalized Biodegradable Poly(Lactide-co-Glycolide Particles Containing Entrapped Antigen for the Induction of Immunological Tolerance", Invention Disclosure Form, Northwestern University received Dec. 17, 2012.
"Determination of Zeta Potential with Two Coating Reagents: Formulation Summary of PLGA Microsphere in the Presence of PVA vs PEMA using Double Emulsion Method", Malvern Instruments, Ltd.
"Determination of Zeta Potential with Two Different Coating Reagents: Formulation Summary of Nanoparticles from Resomer 502 in the Presence of PVA vs PEMA", Supplementary Experimental Evidence.
"Vaccine Protects Against High Doses of Gluten, Research Shows", Beyond Celiac, webpage, Jun. 14, 2019.
Bowdish, D., et al., "MARCO, TLR2, and CD14 Are Required for Macrophage Cytokine Responses to Mycobacterial Trehalose Dimycolate and *Mycobacterium tuberculosis*", PLOS Pathog., 5(6), Jun. 12, 2009, 1-14.

(56) References Cited

OTHER PUBLICATIONS

Danhier, E., et al., "PLGA-Based Nanoparticles: An Overview of Biomedical Applications", J. Control. Release, vol. 161, Feb. 4, 2012, 505-522.

Daveson, J., et al., "Epitope-Specific Immunotherapy Targeting CD4-Positive T Cells in Celiac Disease: Safety, Pharmacokinetics, and Effects on Intestinal Histology and Plasma Cytokines with Escalating Dose Regimens of Nexvax2 in a Randomized, Double-Blind, Placebo-Controlled P", EBioMedicine, vol. 26, Nov. 22, 2017, 78-90.

Dobrovolskaia, M., et al., "Immunological Properties of Engineered Nanomaterials", Nature Nanotech., vol. 2, Aug. 2007, 469-478.

Getts, D. R., et al., "Therapeutic Inflammatory Monocyte Modulation Using Immune-Modifying Microparticles", Sci Transl Med, 6, 2014, 219ra7.

Goel, G., et al., "Cytokine Release and Gastrointestinal Symptoms After Gluten Challenge in Celiac Disease", Sci. Adv., vol. 5, Aug. 7, 2019, 1-14.

Goel, G., et al., "Supplementary Materials for Cytokine Release and Gastrointestinal Symptoms After Gluten Challenge in Celiac Disease", Sci. Adv., vol. 5, Aug. 7, 2019, 1-11.

Honary, S., et al., "Effect of Zeta Potential on the Properties of Nano-Drug Delivery Systems—A Review (Part 1)", Tropical Journal of Pharmaceutical Research , vol. 12, Apr. 2013, 255-264.

Jozefowski, S., et al., "Role of Scavenger Receptor MARCO in Macrophage Responses to CpG Oligodeoxynucleotides", J. Leukocyte Biol., vol. 80, Oct. 2006, 870-879.

Keegan, M., et al., "Biodegradable Microspheres with Enhanced Capacity for Covalently Bound Surface Ligands", Macromol., vol. 37, Nov. 20, 2004, 9779-9784.

Keegan, M., "Biodegradable Microspheres with Enhanced Capacity for Surface Ligand Conjugation", Doctoral dissertation presented to faculty of the Graduate School of Cornell University, 2004, 1-118.

Kelly, C., et al., United Euro. Gastro. J., vol. 7, No. 10, 2019, 1421.

Kelly, C., et al., "TAK-101 Nanoparticles Induce Gluten-Specific Tolerance in Celiac Disease: A Randomized, Double-Blind, Placebo-Controlled Study", Gastroent., vol. 161, No. 1, Jul. 2021, 1-15.

Kim, W., et al., "Suppression of Collagen-Induced Arthritis by Single Administration of Poly(Lactic-Co-Glycolic Acid) Nanoparticles Entrapping Type II Collagen", Arth. & Rheum., vol. 46, No. 4, Apr. 2002, 1109-1120.

Lutsiak, M., et al., "Biodegradable Nanoparticle Delivery of a Th2-Biased Peptide for Induction of Th1 Immune Responses", J. Pharmacy and Pharmacol., vol. 58, Feb. 2006, 739-747.

Marin, E., et al., "Critical Evaluation of Biodegradable Polymers Used in Nanodrugs", Int. J. Nanomed., vol. 8, 2013, 3071-3091.

McCarville, J., et al., "Pharmacological Approaches in Celiac Disease", Curr. Opin. in Pharm., vol. 25, Sep. 27, 2015, 7-12.

McDonald, T., et al., "Subcutaneous Administration of Biotherapeutics: Current Experience in Animal Models", Curr. Opin. Molec. Ther., 12(3), 350-360.

Mitchell, H., et al., "Editorial: A Non-Dietary Treatment for Coeliac Disease—Two Steps Forward, One Step Back?", Alim. Pharacol. & Therapeutics, vol. 50, 2019, 955-965.

Mukhopadhyay, S., et al., "MARCO, An Innate Activation Marker of Macrophages, is a Class A Scavenger Receptor for Neisseria Meningitidis", Eur. J. Immunol., vol. 36, Jan. 24, 2006, 940-949.

Ojala, J., et al., "Crystal Structure of the Cysteine-Rich Domain of Scavenger Receptor MARCO Reveals the Presence of a Basic and an Acidic Cluster that Both Contribute to Ligand Recognition", J. Bio. Chem., vol. 282, No. 22, Jun. 1, 2007, 16654-16666.

Pearson, R., et al., "Overcoming Challenges in Treating Autoimmunity: Development of Tolerogenic Immune- Modifying Nanoparticles", Nanomed: Nanotech., Bio., & Med., vol. 18, 2019, 282-291.

Pecora, R., "Dynamic Light Scattering Measurement particles in Liquids", J. Nanopart. Res., vol. 2, 2000, 123-131.

Senger, S., et al., "Identification of Immunodominant Epitopes of A-Gliadin in HLA-DQ8 Transgenic Mice Following Oral Immunization", J. Immun., 175(12), 2005, 8087-8095.

Sharif, S., et al., "Biodegradable Microparticles as a Delivery System for the Allergens of *Dermatophagoides Pteronyssinus* (house dust mite): I. Preparation and Characterization of Microparticles", Int. J. Pharma., vol. 119, 1995, 239-246.

Sollid, L., et al., "Nomenclature and Listing of Celiac Disease Relevant Gluten T-Cell Epitopes Restricted by HLA-DQ Molecules", Immunogen., vol. 64, 2012, 455-460.

Truitt, K., et al., "Randomised Clinical Trial: A Placebo-Controlled Study of Subcutaneous or Intradermal NEXVAX2, An Investigational Immunomodulatory Peptide Therapy for Coeliac Disease", Aliment. Pharmacol. Ther., vol. 50, 2019, 547-555.

Tye-Din, J., et al., "Comprehensive, Quantitative Mapping of T Cell Epitopes in Gluten in Celiac Disease", Tco. Transl. Med., vol. 2., No. 41, Jul. 21, 2010, 1-14.

Zhang, X., et al., "Preparation and Characterization of Insulin-Loaded Bioadhesive PLGA Nanoparticles for Oral Administration", Euro. J. Pharma. Sci., vol. 45, Jan. 10, 2012, 632-638.

\* cited by examiner

MICROPARTICLES AND NANOPARTICLES HAVING NEGATIVE SURFACE CHARGES

REFERENCE TO RELATED APPLICATIONS

This application is a continuation of U.S. application Ser. No. 14/916,439, filed Mar. 3, 2016, which is a US National stage entry of International Application No. PCT/US2013/073019, which designated the United States and was filed on Dec. 4, 2013, published in English, which claims the benefit of U.S. Provisional Application No. 61/733,216, filed on Dec. 4, 2012. The entire teachings of the above applications are incorporated herein by reference.

BACKGROUND OF THE INVENTION

Certain carboxylated particles, such as carboxylated polystyrene, PLGA, or diamond particles, when administered to subjects, may ameliorate certain conditions, such as pathological inflammatory immune responses (see WO 2012/065153).

Inflammatory diseases and disorders are conditions in which an abnormal or otherwise deregulated inflammatory response contributes to the etiology or severity of disease. Examples include autoimmune diseases such as rheumatoid arthritis, multiple sclerosis, and diabetes, infectious diseases such as tuberculosis and various forms of meningitis and encephalitis including West Nile Virus encephalitis and other disorders include atherosclerosis and ischemic reperfusion.

Many of these diseases are characterized by a mononuclear cell infiltration at a site of tissue injury or other insult. Examples of mononuclear cells that have been observed in these infiltrations include lymphocytes, especially T lymphocytes, and cells of the mononuclear phagocyte system (MPS cells) such as monocytes, macrophages, dendritic cells, microglial cells and others.

However, it is Applicant's belief that carboxylated PLGA particles produced using conventional means are frequently not biocompatible and thus PLGA particles resulting from such manufacturing processes may not be safe for use on humans and animals. In addition, it is Applicant's belief that PLGA particles produced using conventional means may not contain sufficient number of COOH groups for attaching API's or other chemical entities to microparticles and nanoparticles.

There is a need to prepare negatively charged (e.g., carboxylated PLGA) microparticles and nanoparticles with enhanced therapeutic properties.

SUMMARY OF THE INVENTION

One aspect of the invention provides a method for the preparation of a composition comprising microparticles or nanoparticles having negative surface charges, said method comprising producing said microparticles or nanoparticles with a pharmaceutically acceptable polymer using either an emulsion process or a precipitation process: (a) wherein said emulsion process or said precipitation process is carried out in an aqueous solution having a pH that promotes ionization of said pharmaceutically acceptable polymer; (b) wherein said pharmaceutically acceptable polymer has an average molecular weight of from about 500 to about 1,000,000 Da, about 500 to about 50,000 Da, or preferably from about 1,000 to about 50,000 Da, or about 1,000 to about 30,000 Da; and/or, (c) wherein said pharmaceutically acceptable polymer contains multiple negatively charged terminal groups.

In certain embodiments, the emulsion process comprises: (1) dissolving the pharmaceutically acceptable polymer in a first solvent to form a polymer solution; (2) emulsifying the polymer solution in a solution of a second solvent to form an emulsion, wherein the first solvent is not miscible or partially miscible with the second solvent, and wherein the solution of the second solvent optionally comprises a pharmaceutically acceptable negatively charged agent; and, (3) removing the first solvent to form said microparticles or nanoparticles having negative surface charges; wherein said solution of the second solvent is optionally said aqueous solution.

In certain embodiments, the precipitation process comprises: (1) dissolving the pharmaceutically acceptable polymer in a first solvent to form a polymer solution; (2) preparing a solution of a second solvent, wherein the first solvent is miscible with the second solvent, and wherein the solution of the second solvent optionally comprises a pharmaceutically acceptable negatively charged agent and optionally comprises a surfactant; and, (3) combining (e.g., adding) the polymer solution to the solution of the second solvent while mixing, thus forming said microparticles or nanoparticles having negative surface charges; wherein said solution of the second solvent is optionally said aqueous solution.

In certain embodiments, the emulsion process is a double emulsion process comprising: (1) dissolving the pharmaceutically acceptable polymer in a first solvent to form a polymer solution; (2) adding a small amount of a solution of a second solvent to the polymer solution to form a mixture, wherein the first solvent is not miscible or partially miscible with the second solvent, and wherein the solution of the second solvent optionally comprises an active pharmaceutical ingredient (API); (3) emulsifying the mixture to form a first emulsion; (4) emulsifying the first emulsion in the solution of the second solvent to form a second emulsion, wherein the solution of the second solvent optionally comprises a pharmaceutically acceptable negatively charged agent, and optionally further comprises a surfactant; and, (5) removing the first solvent to form said microparticles or nanoparticles having negative surface charges; wherein said solution of the second solvent is optionally said aqueous solution.

In certain embodiments, the pharmaceutically acceptable negatively charged agent is incorporated into said microparticles or nanoparticles to increase negative surface charges on said microparticles or nanoparticles.

In certain embodiments, the pharmaceutically acceptable negatively charged agent is incorporated into said microparticles or nanoparticles to increase the numbers of carboxyl groups on said microparticles or nanoparticles.

In certain embodiments, the pharmaceutically acceptable negatively charged agent comprises polyacrylic acid, or poly(ethylene-alt-maleic acid) (PEMA).

In certain embodiments, the pharmaceutically acceptable polymer is a naturally occurring polymer.

In certain embodiments, the naturally occurring polymer is cellulose, dextrin, hyluronic acid, gelatin, polysaccharide, amino acid, or polyhydroxyalkanoates.

In certain embodiments, the pharmaceutically acceptable polymer is a synthetic polymer.

In certain embodiments, the synthetic polymer is polyacrylic acid, polymethacrylic acid, polylactic acid, polyglycolic acid, polyhydroxybutytic acid, polylactide, polyglycolide, poly(lactide-co-glycolide) polycaprolactone, polyanhydride, or poly(lactide-co-glycolide) or PLGA, or a salt, derivative, copolymer, or mixture thereof. Preferably, the synthetic polymer is a biodegradable polymer.

In certain embodiments, the synthetic polymer is a PLGA polymer having an L/G ratio of from about 95/5 to 5/95, preferably from 85/15 to 15/85, and most preferably about 50/50.

In certain embodiments, the microparticles or nanoparticles have a zeta potential of from about −5 mV to about −200 mV, preferably from about −15 mV to about −100 mV, most preferably from −35 mV to −85 mV.

In certain embodiments, the first solvent is a volatile solvent.

In certain embodiments, the polymer is a PLGA polymer, and the volatile solvent is methylene chloride, ethyl acetate, or chloroform.

In certain embodiments, the solution of the second solvent comprises a surfactant.

In certain embodiments, said solution of the second solvent is a mixture of the first and second solvent. In certain embodiments, the volume ratio of the first solvent to the second solvent in said solution of the second solvent is about 0.1:99.9, about 1:99, about 5:95, about 7.5:92.5; about 7.8:92.2; about 8:92, or about 10:90.

In certain embodiments, the surfactant comprises organic or inorganic pharmaceutical excipients; various polymers; oligomers; natural products; nonionic, cationic, zwitterionic, or ionic surfactants; and mixtures thereof.

In certain embodiments, the polymer is a PLGA polymer, and the surfactant is/comprises polyvinyl alcohol, polyvinylpyrrolidone, a Tween series surfactant, Pluronic F-68, Poloxamer series, or Triton X-100 and its derivatives.

In certain embodiments, the emulsifying step comprises homogenization, mechanical stirring, and/or microfluidization.

In certain embodiments, the first solvent is removed through solvent exchange and/or evaporation.

In certain embodiments, the pharmaceutically acceptable negatively charged agent is a carboxyl-containing agent.

In certain embodiments, the carboxyl-containing agent comprises hyaluronic acid; gelatin; polysaccharide; polyacrylic acid; polymethacrylic acid; hydroxyethylmethacrylic acid; amino acid; or a salt, derivative, copolymer, or mixture thereof.

In certain embodiments, the pH that promotes ionization of the pharmaceutically acceptable polymer is between about 4-14, 6-14, 6-10, or about 8-12.

In certain embodiments, a base (e.g., sodium hydroxide, potassium hydroxide, sodium bicarbonate, sodium carbonate, potassium bicarbonate, or potassium carbonate) is used to adjust pH of the aqueous solution.

In certain embodiments, the second solvent is water, and the first solvent miscible with water is or comprises acetone, tetrahydrofuron (THF), acetonitrile, dimethyl sulfoxide (DMSO), or dimethylformamide (DMF).

In certain embodiments, the multiple negatively charged terminal groups are carboxyl terminal groups.

In certain embodiments, the polymer containing multiple negatively charged carboxyl terminal groups is produced by using a carboxyl-functional initiator in the preparation of the polymer.

In certain embodiments, the carboxyl-functional initiator is an α-hydroxyl acid, preferably lactic acid or glycolic acid.

In certain embodiments, the polymer containing multiple negatively charged carboxyl terminal groups is produced by grafting a carboxyl-containing entity to the polymer.

In certain embodiments, the carboxyl-containing entity is or comprises polyacrylic acid, polymethacrylic acid, poly (hydroxyethyl methacrylic acid), poly(maleic acid), polyanhydrides, or a salt, derivative, copolymer, or mixture thereof.

In certain embodiments, the polymer containing multiple negatively charged carboxyl terminal groups is produced by converting a functional group on the polymer to carboxyl group.

In certain embodiments, the functional group is a hydroxyl group, and wherein the hydroxyl group is converted to the carboxyl group by reacting with an anhydride (e.g., dihydrofuran-2,5-dione).

In certain embodiments, the polymer containing multiple negatively charged carboxyl terminal groups is produced by using an initiator that contains multiple carboxyl groups for generating hyperbranched polymer containing multiple negatively charged carboxyl terminal groups.

In certain embodiments, the microparticles or nanoparticles have average particle sizes of from about 1 nm to about 1000 μm, preferably from about 10 nm to about 100 μm, more preferably from about 20 nm to about 5 μm, and most preferably from about 50 nm to about 2 μm.

In certain embodiments, the pharmaceutically acceptable polymer is PLGA, and wherein the microparticles or nanoparticles are PEGylated.

In certain embodiments, the microparticles or nanoparticles are PEGylated by mixing polyethylene glycol (PEG) or PEG-containing entity during the preparation of the microparticles and nanoparticles.

In certain embodiments, the microparticles or nanoparticles are PEGylated by using copolymers of PEG and PLGA.

In certain embodiments, the microparticles or nanoparticles are PEGylated by physically absorbing PEG polymers or polymers containing PEG units onto the PLGA microparticles and nanoparticles.

In certain embodiments, the microparticles or nanoparticles are PEGylated by conjugating PEG units to the surface of the PLGA microparticles or nanoparticles via covalent bonds.

In certain embodiments, an API (active pharmaceutical ingredient) is covalently attached to the surface of the microparticles or nanoparticles via covalent bonds.

In certain embodiments, the method further comprises chemically conjugating a biomolecule (e.g., a peptide or a protein) to the surface of the microparticles or nanoparticles.

Another aspect of the invention provides a composition comprising microparticles or nanoparticles having negative surface charges, wherein the composition is prepared according to any one of the methods described herein.

In certain embodiments, the composition is free from other API (e.g., attached peptide or antigenic moieties).

Another aspect of the invention provides a pharmaceutical composition comprising any of the subject composition, and a pharmaceutically accepted carrier or excipient.

Another aspect of the invention provides a method of treating a disease or condition in a subject, wherein the disease or condition is treatable with microparticles or nanoparticles with negative surface charge, comprising administering a composition or a pharmaceutical composition comprising the microparticles or nanoparticles to the subject, thereby treating the disease or condition.

In certain embodiments, the disease or condition is characterized by an inflammatory immune response.

In certain embodiments, the disease or condition is multiple sclerosis (MS), psoriasis, rheumatoid arthritis, type 1 diabetes.

In certain embodiments, the method further comprises administering a second therapeutic agent known to be effective for treating the disease or condition.

It should be understood that any embodiments described herein can be combined with any other embodiments, including embodiments described only under one aspect of the invention, and embodiments described only in the examples.

DETAILED DESCRIPTION OF THE INVENTION

This invention described herein provides polymer particles (microparticles and nanoparticles) which contain unusually high or at least increased negative charges on the surface of said particles compared to those produced using conventional methods. Preferably, polymers used for the preparation of the particles are pharmaceutically acceptable materials.

As used herein, "pharmaceutically acceptable" includes those compounds, materials, compositions, and/or dosage forms which are, within the scope of sound medical judgment, suitable for medical or veterinary use when in contact with the tissues of human beings and animals, without causing excessive toxicity, irritation, allergic response, or other problems or complications, commensurate with a reasonable benefit/risk ratio. Preferably, a pharmaceutically acceptable material (e.g., polymer or microparticles/nanoparticles produced therefrom) is suitable or approved for human medical use.

As used herein, "microparticles" are roughly round, sphere, or sphere-like in shape, and are generally within the size range of, e.g., between about 1-1,000 μm, or between about 10-100 μm. The subject microparticles may also include particles that are less likely to clump in vivo.

As used herein, "nanoparticles" are roughly round, sphere, or sphere-like in shape, and are generally within the size range of, e.g., between about 1-1,000 nm, between about 10-1,000 nm, or between about 50-1,000 nm, or between about 100-500 nm. The subject nanoparticles may also include particles that are less likely to clump in vivo.

It is not necessary that each microparticle or nanoparticle be uniform in size, although they are generally of a size sufficient to trigger phagocytosis in an antigen presenting cell (APC) or other MPS cell. Thus in one embodiment, the subject microparticles and nanoparticles have a diameter sufficient to trigger phagocytosis in an antigen presenting cell (APC) or other MPS cell.

As used herein, "about" generally means up to ±10% of the particular term being modified.

The negative charge can be, for example, in the form of a carboxylate, sulfonate, nitrate, fluorate, chloride, iodide, persulfate, and many other negatively charged chemical groups. In certain embodiments, the negative charge is mainly conferred by carboxyl groups. The subject microparticles or nanoparticles having net negative surface charges, and may or may not contain some positive surface charges.

A preferred pharmaceutically acceptable polymer useful for the preparation of the subject microparticles and nanoparticles is PLGA. PLGA is typically prepared by ring-opening polymerization of lactide and glycolide. In this reaction, Stannous octoate is usually used as the catalyst, although other catalysts may also be used. An initiator, such as an alcohol, is often used to initiate the polymerization reaction. If no initiator is intentionally added, trace amount of polar compound containing an active proton, such as alcohol and water, may serve as the initiator. Polymerization usually results in a PLGA polymer with a carboxyl group at the chain terminal, as illustrated below:

Therefore, each PLGA polymer molecule is typically linear, and typically contains a single COOH group at the chain terminal. Consequently, conventional PLGA particles prepared from such PLGA polymers only have small amount of COOH groups on the surface, and the negative charge thereon may not be sufficient for certain uses, such as treating inflammatory diseases. In addition, there may not be sufficient numbers of COOH groups for covalently attaching API's or other chemical moiety such as protein ligands or other targeting agents to the surface of said microparticles and nanoparticles. Such protein ligands or other targeting agents may bind to a receptor or a binding partner on the surface of a target cell, tissue, organ, or location.

The instant invention provides various methods or combinations thereof for producing PLGA particles with additional negatively charged groups (e.g., carboxyl groups) on the PLGA particle surfaces. Such PLGA particles with increased net negative surface charges are particularly useful, for example, to treat certain diseases (such as inflammatory diseases) and to facilitate the conjugation of API's or other chemical entity to the microparticles and nanoparticles.

The invention described herein provides several basic methods for the preparation of particles with highly negative surface charges. These methods are not mutually exclusive, and may be combined with one another to produce additive or even synergistic effects to produce microparticles and nanoparticles with highly negatively charged surfaces.

Thus in one aspect, the invention provides a method for the preparation of a composition comprising microparticles or nanoparticles having negative surface charges, the method comprising producing the microparticles or nanoparticles with a pharmaceutically acceptable polymer using either an emulsion process or a precipitation process, wherein the method comprises any one or more features described below, or combination thereof.

Specifically, one feature of the methods of the invention comprises carrying out the emulsion process or the precipitation process in an aqueous solution having a pH that promotes ionization of the pharmaceutically acceptable polymer. For example, the pharmaceutically acceptable polymer may comprise a carboxyl group that becomes ionized (e.g., carries a negative charge) at a basic pH. In another example, the pharmaceutically acceptable polymer may comprise a chemical moiety having a low pKa such that the moiety becomes ionized at a relatively acidic pH (e.g., pH 5 or 6).

While not wishing to be bound by any particular theory, the ionized groups or moieties, compared to their non-ionized forms, tend more to be exposed on the surface of the eventually formed microparticles or nanoparticles, and tend less to be buried inside the eventually formed microparticles or nanoparticles.

Another feature of the methods of the invention comprises using pharmaceutically acceptable polymers having a low average molecular weight. As described herein, PLGA is typically prepared by ring-opening polymerization of lactide and glycolide using Stannous octoate as the catalyst and an alcohol as an initiator. Polymerization usually results in a linear PLGA polymer with a single carboxyl group at the chain terminal. Thus, by using a PLGA polymer having lower molecular weights, or shorter polymer chains, relatively higher carboxyl group density can be reached in the nanoparticles and microparticles. Here, carboxyl group density can be defined as number of carboxyl groups per gram of polymer.

In certain embodiments, the average molecular weight of the pharmaceutically acceptable polymer is within a desired range.

The low end of the range is preferably no less than about 100, 200, 300, 400, 500, 600, 700, 800, 900, 1000, 1200, 1500, 2000, 2500, or 3000 Da. The desired range can have a low end of any of the above values.

The high end of the range is preferably no more than 50,000, 40,000, 35,000, 30,000, 25,000, 20,000, 15,000, 10,000, 7,500, or 5,000 Da. The desired range can have a high end of any of the above values.

values, etc.) potentially negatively charged terminal groups. In certain embodiments, the multiple negatively charged terminal groups are carboxyl terminal groups.

Polymers containing multiple carboxyl groups can be obtained by a variety of means, including: 1) using a carboxyl-functional initiator in the preparation of the polymer. Common carboxyl-functional initiators include but are not limited to α-hydroxyl acid. For example, lactic acid, glycolic acid; 2) grafting carboxyl-containing entities to the polymer chain; 3) converting other functional groups on the PLGA polymer to carboxyl groups via a chemical reaction. For example, hydroxyl groups on PLGA polymers may be converted to carboxyl groups by reacting the hydroxyl groups with an anhydride (e.g., dihydrofuran-2,5-dione). An exemplary reaction is depicted in the scheme below:

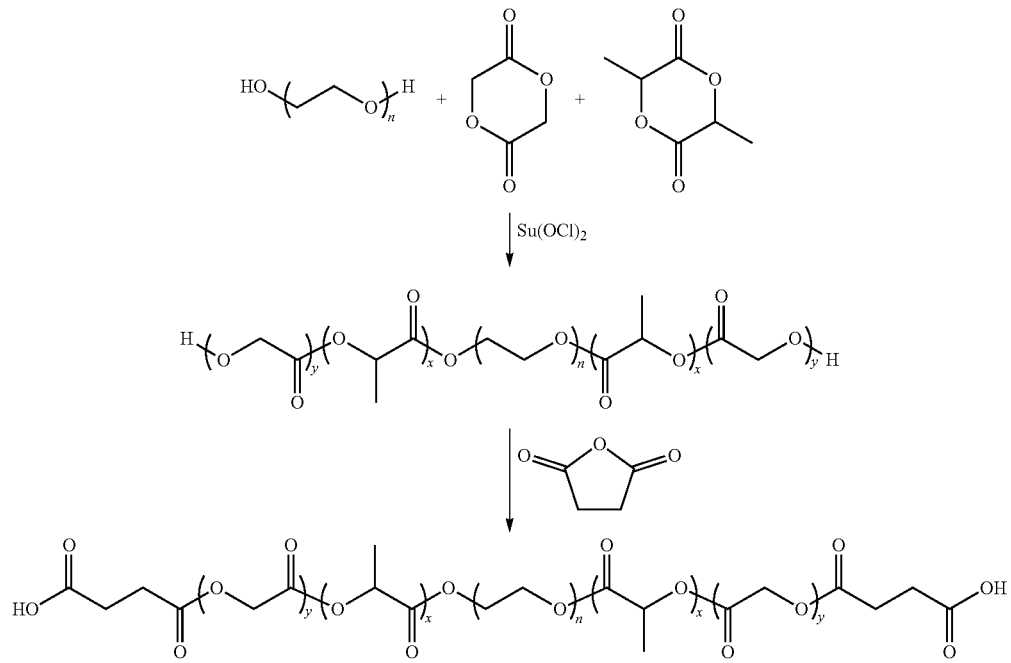

For instance, the desired range may be from about 500 to about 50,000 Da, or from about 1,000 to about 30,000 Da.

In certain pharmaceutically acceptable polymers, such as PLGA, average molecular weight is expressed in other physical properties such as inherent viscosity. Inherent Viscosity (IV) is a viscometric method for measuring molecular size. IV is based on the flow time of a polymer solution through a narrow capillary relative to the flow time of the pure solvent through the capillary. For certainly measures in the instant application, the solvent used is typically chloroform, and the polymer concentration is about 0.5% (w/v). The temperature at which the viscosity is measured is about 30° C. The units of IV are typically reported in deciliters per gram (dL/g). Thus, for example, the desired pharmaceutically acceptable polymer (such as PLGA) that may be used in the instant invention may have an inherent viscosity of from about 0.01 to about 20 dL/g, or from about 0.05 to about 2.0 dL/g.

Yet another feature of the methods of the invention comprises using pharmaceutically acceptable polymers containing multiple (i.e., two or more, ≥2, ≥3, ≥4, ≥5, ≥10, ≥20, ≥50, ≥75, ≥100, or a range between any of the two recited and, 4) using hyperbranched PLGA polymers that contain multiple carboxyl-containing arms obtained by, for example, using an initiator that contains multiple carboxyl groups on its molecule.

The number of carboxyl group on each (PLGA) polymer is preferably from 1 to 100, more preferably from 2 to 10 (e.g., 2, 3, 4, 5, 6, 7, 8, 9, or 10).

The methods of the invention can comprise any one or more features described herein.

Any art-recognized emulsion process may be used in the methods of the invention. In certain embodiments, the subject microparticles and nanoparticles (e.g., PLGA microparticles and nanoparticles) can be prepared by an emulsification process comprising the following steps (not necessarily in this order): 1) dissolving the pharmaceutically acceptable polymer (e.g., PLGA) in a first solvent (e.g., methylene chloride) to form a polymer solution; 2) emulsifying the polymer solution (e.g., PLGA solution) in a solution of a second solvent (e.g., an aqueous solution, or an organic solvent) to form an emulsion, wherein the first solvent is not miscible or partially miscible with the second solvent, and wherein the solution of the second solvent optionally comprises a pharmaceutically acceptable negatively charged agent; and, 3) removing the first solvent to form the microparticles or nanoparticles having negative surface charges, wherein the solution of the second solvent is optionally the aqueous solution.

In certain embodiments, in the emulsification process, the weight ratio of the PLGA solution to the aqueous solution is typically from 1:1,000 to 10:1, preferable from 1:100 to 1:1.

As used herein, miscibility is defined to be the property of liquids to mix in all proportions, forming a homogeneous solution. Substances/liquids are said to be immiscible or not miscible, if in some proportion, they do not form a solution.

Exemplary solvents miscible with water include acetone, tetrahydrofuron (THF), acetonitrile, dimethyl sulfoxide (DMSO), dimethylformamide (DMF).

Another art-recognized emulsion process is commonly known as double emulsion process, which may be particularly useful when an active pharmaceutical ingredient (API), such as a protein-based therapeutics prepared in an aqueous solution, is first emulsified with a pharmaceutically acceptable polymer solution to form a first emulsion such that the protein-based therapeutics is encapsulated within the polymer solution. Then the polymer, and the therapeutics encapsulated therein, is again emulsified in a larger volume of solvent to form a second emulsion (e.g., the water-in-oil-in-water or w/o/w type double emulsion), before the microparticle or nanoparticle is formed.

For example, in the above described w/o/w technique, a relatively small amount of aqueous protein solution may be introduced into a relatively larger amount of organic solvent, such as methylene chloride or ethyl acetate, that dissolves the hydrophobic polymer PLGA. The first emulsion is then formed using a suitable method, e.g., probe sonication or homogenization. After formation of the first emulsion, a second emulsion is formed by introducing the first emulsion into an aqueous solution containing an emulsifier, e.g., polyvinyl alcohol. Again, a homogenization method is used to form the second emulsion. This is next followed by a period of solvent evaporation leading to the hardening of the polymer, typically by stirring for some hours. As a result, the protein solution is trapped into the relative hydrophobic matrix of the PLGA polymer forming small inclusions. Finally, the microparticles ornanoparticles formed are collected, washed (e.g., with distilled water) via repeated centrifugation or filtration, followed by dehydration, typically by lyophilization.

Thus in certain embodiments, the subject microparticles and nanoparticles (e.g., PLGA microparticles and nanoparticles) can be prepared by a double emulsification process comprising the following steps (not necessarily in this order): 1) dissolving the pharmaceutically acceptable polymer (e.g., PLGA) in a first solvent (e.g., methylene chloride) to form a polymer solution; 2) adding a relatively small amount of a solution of a second solvent into the polymer solution to form a mixture, wherein the first solvent is not miscible or partially miscible with the second solvent, and wherein the solution of the second solvent optionally comprises an active pharmaceutical ingredient (API); 3) emulsifying the mixture to form a first emulsion; 4) emulsifying the first emulsion in the solution of the second solvent to form a second emulsion, wherein the solution of the second solvent optionally comprises a pharmaceutically acceptable negatively charged agent, and optionally further comprises a surfactant; and, 5) removing the first solvent to form said microparticles or nanoparticles having negative surface charges; wherein said solution of the second solvent is optionally said aqueous solution.

In certain embodiments, the volume of the small amount of the solution of the second solvent added to the polymer solution for the generation of the first emulsion is typically from 0.01% to 50%, preferable from 0.1% to 10%, based on the volume of the PLGA solution.

In certain embodiments, the volume ratio of the first emulsion to the solution of the second solvent described as in Step 4) above is typically from 10:1 to 1:10,000, preferably from 1:1 to 1:100.

Any art-recognized precipitation process may be used in the methods of the invention. In certain embodiments, the subject microparticles and nanoparticles (e.g., PLGA microparticles and nanoparticles) can be prepared by a precipitation process comprising the following steps (not necessarily in this order): 1) dissolving the pharmaceutically acceptable polymer (e.g., PLGA) in a first solvent (e.g., acetone) to form a polymer solution; 2) preparing a solution of a second solvent (e.g., aqueous solution, such as 1 mM NaOH solution), wherein the first solvent is miscible with the second solvent, and wherein the solution of the second solvent optionally comprises a pharmaceutically acceptable negatively charged agent and optionally comprises a surfactant; and, 3) adding the polymer solution to the solution of the second solvent while mixing, thus forming the microparticles or nanoparticles having negative surface charges; wherein the solution of the second solvent is optionally the aqueous solution.

In certain embodiments, in the precipitation process, the volume ratio of the PLGA solution to the aqueous solution is typically from 10:1 to 1:1,000, preferably from 1:1 to 1:10.

In certain embodiments, as an alternative procedure to Step 3) in the precipitation process, the solution of the second solvent (e.g., the aqueous solution) can be added to the polymer solution (e.g., PLGA solution).

In any of the above embodiments, the pharmaceutically acceptable negatively charged agent may cover the surface of the microparticles or nanoparticles, and/or be at least partially incorporated into said microparticles or nanoparticles to increase negative surface charges on the microparticles or nanoparticles. Representative pharmaceutically acceptable negatively charged agent may comprise polyacrylic acid, or poly(ethylene-alt-maleic acid) (PEMA).

In any of the aspects described above, while numerous types of carboxylated particles can ameliorate inflammatory immune responses, it is necessary to use particles that are made of materials that are pharmaceutically acceptable. These pharmaceutically acceptable polymers may be of natural or synthetic origin. Examples of naturally occurring polymers include but are not limited to cellulose, dextrin, hyaluronic acid, gelatin, polysaccharides, amino acid, polyhydroxyalkanoates, etc.

Synthetic polymers useful for the instant invention are typically biocompatible and/or biodegradable, and are therefore safe for human and animal use. Examples of the synthetic polymers useful for the invention include polymers such as polyacrylic acid, polymethacrylic acid, polylactic acid, polyglycolic acid, polyhydroxybutytic acid, polylactide, polyglycolide, poly(lactide-co-glycolide) polycaprolactone, polyanhydrides, etc. Poly(lactide-co-glycolide) or PLGA is a preferred material for the preparation of the subject negatively charged particles.

The composition and biodegradability of the subject PLGA polymer is partly determined by the molar ratio of lactide (L) to glycolide (G) unit in the polymer, or L/G ratio. The L/G ratio of the PLGA polymer in the present invention can be from 100/0 to 0/100. As used herein, an L/G ratio of "100/0" refers to polylactide or PLA, and an L/G ratio of "0/100" refers to polyglycolide, or PGA. Preferably the L/G ratio for the PLGA polymer is from about 95/5 to 5/95, more preferably from about 85/15 to 15/85. The most preferable L/G ratio in the present invention is about 50/50.

Other polymers can be mixed with the PLGA polymer in the preparation of the PLGA microparticles and nanoparticles. For example, polyethylene glycol, or PEG, is often added to the PLGA for enhanced performance. PEGylated particles are useful because they often have increased circulation time in human or animal bodies.

In certain embodiments, copolymers of PEG and PLGA can also be used.

The microparticles and nanoparticles prepared from the PEG and PLGA mixture or PEG and PLGA copolymer are referred to as PEGylated PLGA microparticles and nanoparticles.

Such "PEGylation" process can also be done after microparticles and nanoparticles are formed. In this case, PEG polymers or other polymers containing PEG units are coated via physical absorption onto the PLGA microparticles and nanoparticles.

The PEG units can also be attached to the surface of PLGA microparticles or nanoparticles via covalent bonds. Such process is often referred to as "conjugation." In a conjugation process, a reactive entity containing PEG units react with certain functional groups on the surface of the microparticles and nanoparticles to form chemical bonds.

Thus in certain embodiments, the pharmaceutically acceptable polymer is PLGA, and the microparticles or nanoparticles are PEGylated. The microparticles or nanoparticles may be PEGylated by mixing polyethylene glycol (PEG) or PEG-containing entity during the preparation of the microparticles and nanoparticles. The microparticles or nanoparticles may also be PEGylated by using copolymers of PEG and PLGA. The microparticles or nanoparticles can further be PEGylated by physically absorbing PEG polymers or polymers containing PEG units onto the PLGA microparticles and nanoparticles. The microparticles or nanoparticles may additionally be PEGylated by conjugating PEG units to the surface of the PLGA microparticles or nanoparticles via covalent bonds.

The pharmaceutically acceptable negatively charged agent may be a pharmaceutically acceptable carboxyl-containing agent, such as one useful for producing (PLGA) microparticles and nanoparticles with additional amount of carboxyl groups on the surface. Such carboxyl-containing agent includes but is not limited to hyaluronic acid or analogs or derivative thereof, gelatin, polysaccharides, hydroxyethylmethacrylic acid, polyacrylic acid, polymethacrylic acid, amino acids, or their salts, derivatives, copolymers and mixtures.

The amount of the pharmaceutically acceptable negatively charged agent used in the current invention is from 0.01% to 30%, preferably from 0.1% to 5%, based on the weight of the pharmaceutically acceptable polymer (such as PLGA) used in the formulation.

Hyaluronic acid analogs include many natural polysaccharides that have been sulphated, which may behave like sulphated glycosaminoglycan, such as heparin (Hoffman et al., 1982, *Carbohydrate Res.*, 2:115; Kindness et al., 1980, *Brit. J. Pharmac.*, 69:675; Horton et al., 1973, *Carbohydrate Res.*, 30:349; Okada et al., 1979, *Makromol. Chem.* 180:813; Kikuchi et al., 1979, *Nippon Kagaku Kaishi*, 1:127; Manzac et al., 1981, *Proc. Third M.I.S.A.O.*, 5:504). Moreover, sulphuric, carboxy or sulphonated groups have been attached to synthetic polymers such as polystyrene (Kanmaugue et al., 1985, *Biomaterials*, 6:297) and polyurethanes (Ito et al., 1992, *Biomaterials*, 13:131), which may be used as HA analogs in the instant invention. The high density of the negative charges on these HA analogs (e.g., the N-sulphated group of the glucosamine residues), which may be pH-dependent, confers additional benefit when added to the subject micro-/nano-particles as HA analogs.

The HA analogs can be produced by chemical reactions known for the sulphation of polysaccharides (see, e.g., WO 88/00211; EP 0340628; *Carbohydrate Research*, 158:183-190, 1986).

An important family of HA analogs include HA derivatives produced by modification of hyaluronic acid.

Certain hyaluronic acid derivatives are known in the art. For example, WO 95/25751 (incorporated by reference) describes various heparin-like sulphated polysaccharide derivatives, such as sulphated hyaluronic acid of different molecular weight ranges, such that the number of sulfate groups per repetitive unit is in the range of from 0.5 to 3.5. The sulphated HA not only contains more negative charges per repeat unit, but also inhibits the production of tumor necrosis factor (TNF) when the sulphated hyaluronic acid having a molecular weight in the range of between about 10,000 and about 50,000 Daltons is used. Excessive TNFα activity is associated with the proliferation of inflammatory cells, and is the cause of many inflammatory disease conditions. Thus using such sulfated hyaluronic acid can further enhance the anti-inflammatory effect of the subject micro-/nano-particles.

Preferably, the sulfated hyaluronic acid has a molecular weight in the range between about 10,000 and about 50,000 Daltons, or between about 50,000 and about 250,000 Daltons, or between about 250,009 and about 750,000 Daltons, or between about 750,000 and about 1,250,000 Daltons, wherein in each case, the degree of sulfation of said sulfated hyaluronic acid is 2.5, 3.0 or 3.5 sulfate groups per repetitive unit of hyaluronic acid.

WO 1998/045335A1 describes certain biocompatible sulphated compounds of hyaluronic acid and derivatives thereof, optionally salified, wherein the glucosamines are partially N-sulphated, or partially N-sulphated and partially or totally O-sulphated in position 6. Specifically, such HA derivatives are obtained by means of a controlled sulphation reaction of the amino group of the glucosamine of hyaluronic acid, previously N-deacetylated according to the procedure described by P. Shaklee (1984) *Biochem. J.*, 217:187-197 (incorporated herein). Apart from their biocompatibility characteristics, such N-sulphated derivatives also has antiviral activity, anti-inflammatory activity, anti-thrombotic and anticoagulant properties.

In certain embodiments, the degree of sulphation per one dimeric unit of the amino groups varies between 1 and 70% and that of the hydroxyl group in position 6 varies between 0 and 100%. In certain embodiments, the degree of sulphation per one dimeric unit of the amino groups varies between 5 and 40% and that of the hydroxyl group in position 6 varies between 0 and 100%.

Additional hyaluronic acid derivatives are described in U.S. Pat. No. 7,993,678, which derivatives have at least one hydroxyl-group of hyaluronic acid is substituted, through a reaction with aryl/alkyl succinic anhydrides (ASA), to produce aryl/alkyl succinic anhydride HA derivatives. The derivative carries more negative charge per repeat unit, and can be used with or in place of HA in the methods of the invention.

In certain embodiments, the hyaluronic acid analogs or derivatives are no more than 10, 15, 20, 25, or 30% (w/w) of the pharmaceutically acceptable polymer.

In certain embodiments, the microparticles or nanoparticles have a negative (surface) charge. The negative charge density on the carboxylated microparticles and nanoparticles can be quantified by zeta potential. The zeta potential of the carboxylated microparticles and nanoparticles is typically measured in an aqueous suspension of the particles at a pH of from 4 to 10, preferably from 5 to 8. In certain embodiments, the microparticles or nanoparticles produced by the methods of the invention may have a zeta potential of from about −5 mV to about −200 mV, preferably from about −15 mV to about −100 mV, most preferably from −35 mV to −85 mV.

The solvent used in the dissolving step for the polymer can be any type of solvent that dissolves the polymer (e.g., PLGA). However, a volatile solvent is preferably used for its removal. For example, preferred solvents for forming the PLGA solution include methylene chloride, ethyl acetate, and chloroform.

In the emulsifying step, the (aqueous) solution may contain a surfactant or surface stabilizer. Surfactants generally include compounds that lower the surface tension of a liquid, the interfacial tension between two liquids, or that between a liquid and a solid. Surfactants may act as detergents, wetting agents, emulsifiers, foaming agents, and dispersants. Surfactants are usually organic compounds that are amphiphilic, which contain both hydrophobic groups (usually branched, linear, or aromatic hydrocarbon chain(s), fluorocarbon chain(s), or siloxane chain(s) as "tail(s)") and hydrophilic groups (usually heads). Surfactants are most commonly classified according to their polar head group: a non-ionic surfactant has no charge groups in its head; an ionic surfactant carries a net charge—if the charge is negative, the surfactant is anionic, and if the charge is positive, it is cationic. If a surfactant contains a head with two oppositely charged groups, it is termed zwitterionic. In certain embodiments, anionic or zwitterionic surfactants, such as those containing carboxyl groups ("carboxylates"), are preferably used in the instant invention. The carboxylates are the most common surfactants and comprise the alkyl carboxylates, such as sodium stearate, sodium lauroyl sarcosinate, and carboxylate-based fluorosurfactants such as perfluorononanoate, perfluorooctanoate (PFOA or PFO).

While not wishing to be bound by any particular theory, surfactant may be useful for the formation and stabilization of the emulsion droplets. The surfactant may also comprise organic or inorganic pharmaceutical excipients, various polymers, oligomers, natural products, nonionic, cationic, zwitterionic, or ionic surfactants, and mixtures thereof.

The surfactants that can be used for the preparation of the subject (PLGA) microparticles/nanoparticles include polyvinyl alcohol, polyvinylpyrrolidone, Tween series, Pluronic series, Poloxamer series, Triton X-100, etc. Additional suitable surfactants are provided herein below.

The emulsification process may be carried out by any art-recognized means, such as homogenization, mechanical stirring, or microfluidization, etc.

The removal of solvent is usually achieved by, for example, solvent exchange and evaporation.

In certain embodiments, in order to ensure that most carboxyl groups are present on the surface of the subject (e.g., PLGA) microparticles and nanoparticles, the aqueous solution is adjusted to a pH that promotes ionization of a moiety on the polymer, such as a basic pH for a carboxyl group on PLGA. The pH is preferably in the range of about 4-14, 6-14, 6-10, or about 8-12, depending on the pKa of the polymer group that can become ionized to carry a negative charge. The pH of the aqueous solution can be adjusted to the preferred range by adding, for example, a base or a solution thereof, such as sodium hydroxide, potassium hydroxide, sodium bicarbonate, sodium carbonate, potassium bicarbonate, potassium carbonate, etc.

The size of the subject microparticles and nanoparticles is from about 1 nm to about 1000 μm, preferably from about 10 nm to about 100 μm, and most preferably from about 20 nm to about 5 μm. For example, the microparticles and nanoparticles may have an average size of about 100, 300, 500, or 700 nm.

As used herein, particle size can be determined by any conventional particle size measuring techniques well known to those skilled in the art. Such techniques include, for example, sedimentation field flow fractionation, photon correlation spectroscopy, light scattering, dynamic light scattering, light diffraction, and disk centrifugation.

Combinations of more than one surfactant can be used in the invention. Useful surfactants or surface stabilizers which can be employed in the invention may include, but are not limited to, known organic and inorganic pharmaceutical excipients. Such excipients include various polymers, low molecular weight oligomers, natural products, and surfactants. Surfactants or surface stabilizers include nonionic, cationic, zwitterionic, and ionic surfactants.

Representative examples of other useful surfactants or surface stabilizers include hydroxypropyl methylcellulose, hydroxypropylcellulose, polyvinylpyrrolidone, sodium lauryl sulfate, sodium dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40(Croda, Inc.); and SA9OHCO, which is $C_{18}H_{37}CH_2(CON(CH_3)\text{-}CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-p-D- glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, and the like.

Examples of useful cationic surfactants or surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N4Amino (Polyethylene Glycol)2000] (sodium salt) (also known as DPPE-PEG(2000)-Amine Na) (Avanti Polar Lipids, Alabaster, Al), Poly(2-methacryloxyethyl trimethylammonium bromide) (Polysciences, Inc., Warrington, Pa.) (also known as S1001), poloxamines such as Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quaternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, C12-15dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)4 ammonium chloride or bromide, N-alkyl (C12-18)dimethylbenzyl ammonium chloride, N-alkyl (C14-18)dimethyl-benzyl ammonium chloride, N-tetradecylidmethylbenzyl ammonium chloride monohydrate, dimethyl didecyl ammonium chloride, N-alkyl and (C12-14) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl(C12-14) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, C12, C15, C17 trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surfactants or surface stabilizers and other useful cationic surfactants or surface stabilizers are described in J. Cross and E. Singer, Cationic Surfactants: Analytical and Biological Evaluation (Marcel Dekker, 1994); P. and D. Rubingh (Editor), Cationic Surfactants: Physical Chemistry (Marcel Dekker, 1991); and J. Richmond, Cationic Surfactants: Organic Chemistry, (Marcel Dekker, 1990), each of which is incorporated by reference herein in its entirety.

Nonpolymeric cationic surfactants or surface stabilizers are any nonpolymeric compound, such as benzalkonium chloride, a carbonium compound, a phosphonium compound, an oxonium compound, a halonium compound, a cationic organometallic compound, a quaternary phosphorous compound, a pyridinium compound, an anilinium compound, an ammonium compound, a hydroxylammonium compound, a primary ammonium compound, a secondary ammonium compound, a tertiary ammonium compound, and quaternary ammonium compounds of the formula NR1R2R3R4(+). For compounds of the formula NR1R2R3R4(+): (i) none of R1-R4 are CH3; (ii) one of R1-R4 is CH$_3$; (iii) three of R1-R4 are CH3; (iv) all of R1-R4 are CH3; (v) two of R1-R4 are CH3, one of R1-R4 is C6H5CH2, and one of R1-R4 is an alkyl chain of seven carbon atoms or less; (vi) two of R1-R4 are CH3, one of R1-R4 is C6H5CH2, and one of R1-R4 is an alkyl chain of nineteen carbon atoms or more; (vii) two of R1-R4 are CH3 and one of R1-R4 is the group C6H5 (CH2)n, where n>1; (viii) two of R1-R4 are CH3, one of R1-R4 is C6H5CH2, and one of R1-R4 comprises at least one heteroatom; (ix) two of R1-R4 are CH3, one of R1-R4 is C6H5CH2, and one of R1-R4 comprises at least one halogen; (x) two of R1-R4 are CH3, one of R1-R4 is C6H5CH2, and one of R1-R4 comprises at least one cyclic fragment; (xi) two of R1-R4 are CH3 and one of R1-R4 is a phenyl ring; or (xii) two of R1-R4 are CH3 and two of R1-R4 are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surfactants or surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surfactants or surface stabilizers are commercially available and/or can be prepared by techniques known in the art.

In certain embodiments, the surface of the subject microparticle or nanoparticle is composed of a material that minimizes nonspecific or unwanted biological interactions between the particle surface and the interstitium, e.g., the particle surface may be coated with a material to prevent or decrease non-specific interactions. Steric stabilization by coating particles with hydrophilic layers such as poly(ethylene glycol) (PEG) and its copolymers such as PLURONICS (including copolymers of poly(ethylene glycol)-bl-poly (propylene glycol)-bl-poly(ethylene glycol)) may reduce the non-specific interactions with proteins of the interstitium as demonstrated by improved lymphatic uptake following subcutaneous injections.

In yet another embodiment, particles of the present invention may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez et al., *Science*, 1998, 281:2013; Niemeyer, C. M., *Angew. Chem. Int. Ed.*, 2003, 42:5796; Waggoner, A. *Methods Enzymol.*, 1995, 246:362; Brus, L. E., *J. Chem. Phys.*, 1993, 79, 5566). Quantum dots, such as hybrid organic/inorganic quantum dots based on a class of polymers known as dendrimers, may be used in biological labeling, imaging, and optical biosensing systems (Lemon et al., *J. Am. Chem. Soc.*, 2000, 122:12886). Unlike the traditional synthesis of inorganic quantum dots, the synthesis of these hybrid quantum dot nanoparticles does not require high temperatures or highly toxic, unstable reagents. (Etienne et al, *Appl. Phys. Lett.*, 87:181913, 2005).

Another aspect of the invention provides a composition comprising the subject microparticles or nanoparticles having negative surface charges, wherein the composition is prepared according to any one of the subject methods described herein or combinations thereof.

In certain embodiments, the composition is free from other active pharmaceutical ingredients or API, such as attached peptide or antigenic moieties.

In certain other embodiments, the composition comprises an API, and the API is covalently attached to the surface of the microparticles or nanoparticles via covalent bonds, such as a bond formed between an amide group of a protein and a carboxyl group on the surface of the microparticle or nanoparticle.

In certain embodiments, the amount of the API may be about 0.01-50% (w/w) of the microparticle or nanoparticle, or about 0.05-25%, about 0.1-10%, about 0.2-5%, 0.5-3%, 1-5%, or 2-5% (w/w) of the microparticle or nanoparticle.

In certain other embodiments, the composition comprises, in place of an API, a targeting moiety, such as a peptide or protein ligand or domain, covalently attached to the surface of the microparticles or nanoparticles, which targeting moiety specifically or preferentially binds to a target site (such as a cell surface receptor or binding partner for the targeting moiety), such that the micro- or nanoparticle bearing such a targeting moiety will be specifically or preferentially directed to the target site in vivo. The targeting moiety bearing micro- or nanoparticle may further comprise an API that is encapsulated or embedded within the micro- or nanoparticle that can be released or otherwise effective at the target site.

A related aspect of the invention provides a pharmaceutical composition comprising the subject composition, and a pharmaceutically accepted carrier or excipient. Pharmaceutical compositions are described below in more details in a separate section.

A further aspect of the invention provides a method of treating a disease or condition in a subject in need thereof, or a method of reducing the duration or severity of the disease or condition in the subject in need thereof, wherein the disease or condition is treatable with microparticles or nanoparticles with negative surface charge, comprising administering a composition or a pharmaceutical composition comprising the microparticles or nanoparticles to the subject, thereby treating the disease or condition.

In a related aspect, the invention provides a method of regulating an immune response in a subject in need thereof, preferably a mammal, more preferably a human, comprising administering a composition or a pharmaceutical composition comprising the microparticles or nanoparticles to the subject, thereby regulating the immune response. Methods of immunoregulation provided by the invention include those that suppress and/or inhibit an innate immune response or an adaptive immune response, including, but not limited to, an immune response stimulated by immunostimulatory polypeptides or viral or bacterial components. The subject particles are administered in an amount sufficient to regulate the immune response. As described herein, regulation of an immune response may be humoral and/or cellular, and is measured using standard techniques in the art and as described herein.

In certain embodiments, the disease or condition is characterized by an inflammatory immune response.

Treatable diseases or conditions include, but are not limited to: an autoimmune disorder, such as multiple sclerosis, scleroderma, type-I diabetes, rheumatoid arthritis, thyroiditis, systemic lupus erythmatosis, Reynauud's syndrome, Sjorgen's syndrome, autoimmune uveitis, autoimmune myocarditis, or Crohn's disease. In a particular embodiment, the autoimmune disease is multiple sclerosis. An individual having an autoimmune disease or inflammatory disease is an individual with a recognizable symptom of an existing autoimmune disease or inflammatory disease.

Autoimmune diseases can be divided in two broad categories: organ-specific and systemic. Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus *foliaceus*, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism.

Autoimmune diseases may also include, without limitation, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barré syndrome, chronic inflammatory demyelinating polyradiculoneuropathy, multifocal motor neuropathy with conduction block, chronic neuropathy with monoclonal gammopathy, opsoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Behcet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in *Harrison's Principles of Internal Medicine*, 14th edition, Fauci, A. S. et al., Eds., New York: McGraw-Hill, 1998.

In another embodiment, the diseases or conditions include an allergic disorder or condition, such as allergic disease, allergy, eczema, asthma, allergic rhinitis or skin hypersensitivity. An individual having an allergic disease or asthma is an individual with a recognizable symptom of an existing allergic disease or asthma.

In another embodiment, the diseases or conditions include bacterial or viral infection. An individual having a bacterial or viral infection is an individual with a recognizable symptom of an existing bacterial or viral infection.

In one embodiment, the subject has a viral infection. In a further embodiment, the viral infection is a herpes virus infection, a hepatitis virus infection, a West Nile virus infection, a flavivirus, an influenza infection, a rhinovirus infection, a papillomavirus infection, a paramyxovirus infection, or a parainfluenza virus infection. In a further embodiment, the viral infection infects the central nervous system of said subject. In still a further embodiment, the viral infection causes viral encephalitis or viral meningitis.

In one embodiment, the subject has a bacterial infection. A non-limiting list of bacterial infections treatable with the subject particles of the current invention include *staphylococcus* infections, *streptococcus* infections, mycobacterial infections, *bacillus* infections, *Salmonella* infections, *Vibrio* infections, spirochete infections, and *Neisseria* infections. Preferred are bacteria that infect the central nervous system of the subject. Most preferred are bacteria that cause encephalitis or meningitis.

In one embodiment, the method of the invention induces immune tolerance when administered to a subject with a bacterial or viral infection. In a further embodiment, the method ameliorates or dampens an inflammatory immune response when administered to a subject with a bacterial or viral infection.

In yet another embodiment, the subject is a transplant recipient. Transplantation refers to the transfer of a tissue sample or graft from a donor individual to a recipient individual, and is frequently performed on human recipients who need the tissue in order to restore a physiological function provided by the tissue. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

A serious potential complication of any transplantation ensues from antigenic differences between the host recipient and the engrafted tissue. Depending on the nature and degree of the difference, there may be a risk of an immunological assault of the graft by the host, or of the host by the graft, or both, may occur. The extent of the risk is determined by following the response pattern in a population of similarly treated subjects with a similar phenotype, and correlating the various possible contributing factors according to well accepted clinical procedures. The immunological assault may be the result of a preexisting immunological response (such as preformed antibody), or one that is initiated about the time of transplantation (such as the generation of TH cells). Antibody, T helper (TH) cells, or cytotoxic T (Tc) cells may be involved in any combination with each other and with various effector molecules and cells. However, the antigens which are involved in the immune response are generally not known, therefore posing difficulties in designing antigen-specific therapies or inducing antigen-specific tolerance. The modified particles of the current invention are particularly useful in preventing the rejection of organs because no attached peptides or antigens need to be conjugated to the modified particles in order for the particles to be effective in inducing tolerance or ameliorate an inflammatory immune response.

Certain embodiments of the invention relate to decreasing the risk of host versus graft disease, leading to rejection of the tissue graft by the recipient. The treatment may be performed to prevent or reduce the effect of a hyperacute, acute, or chronic rejection response. Treatment is preferentially initiated sufficiently far in advance of the transplant so that tolerance will be in place when the graft is installed; but where this is not possible, treatment can be initiated simultaneously with or following the transplant. Regardless of the time of initiation, treatment will generally continue at regular intervals for at least the first month following transplant. Follow-up doses may not be required if a sufficient accommodation of the graft occurs, but can be resumed if there is any evidence of rejection or inflammation of the graft. Of course, the tolerization procedures of this invention may be combined with other forms of immunosuppression to achieve an even lower level of risk.

In another embodiment, the diseases or conditions include unwanted immune activation, such as atherosclerosis, ischemic reperfusion injury, and myocardial infarction.

In yet another embodiment, the invention relates to treatment of pathological conditions pertaining to an unwanted hypersensitivity. The hypersensitivity can be any one of types I, II, III, and IV, Immediate (type I) hypersensitivity. The frequency of administration will typically correspond with the timing of allergen exposure. Suitable animal models are known in the art (for example, Gundel et al., *Am. Rev. Respir. Dis.*, 146:369, 1992, Wada et al, *J. Med. Chem.*, 39:2055, 1996; and WO 96/35418).

In certain embodiments, treatable diseases or conditions include those initiated by inflammatory monocytes, autoimmunity, cardiovascular disease (such as cardiac ischemia, or ischemia-reperfusion injury following cardiac infarction and transplantation), viral encephalitis, multiple sclerosis (MS), inflammatory bowel disease (IBD), peritonitis, lethal flavivirus encephalitis, immunopathological viral infections (including Influenza and West Nile Virus (WNV)), rheumatoid arthritis, HIV encephalitis, chronic liver disease, atherosclerosis, cardiac infarction, experimental autoimmune encephalomyelitis (EAE) and its corresponding diseases, Colitis, ulcerative colitis, etc.

In certain embodiments, the microparticle or nanoparticle of the invention (e.g., those produced with the methods of the invention) can be used in combination with a second therapeutic that is effective for treating any one of the treatable conditions.

In certain embodiments, the subject is a human patient. In certain embodiments, the subject is a non-human mammal, such as a non-human primate, a livestock animal (horse, mule, cattle, bull, cow, sheep, goat, pig, camel, etc.), a rodent (rabbit, hamster, mouse, rat, etc.), or a pet (cat, dog).

In one embodiment, the method includes administering the subject composition or pharmaceutical composition comprising the subject microparticles or nanoparticles (e.g., the carboxylated particles) by any suitable means or routes, such as orally, nasally, intravenously, intramuscularly, ocularly, transdermally, or subcutaneously. In a particular embodiment, the particles are administered nasally. In still another embodiment, the particles are administered intravenously.

The particles of the present invention can be given in any dose effective to dampen the inflammatory immune response in a subject in need thereof or to treat a bacterial or viral infection in a subject in need thereof. In certain embodiments, about $10^2$ to about $10^{20}$ particles are provided to the individual. In a further embodiment, between about $10^3$ to about $10^{15}$ particles are provided. In yet a further embodiment, between about $10^6$ to about $10^{12}$ particles are provided. In still a further embodiment, between about $10^8$ to about $10^{10}$ particles are provided. In one embodiment, the preferred dose is 0.1% solids/ml. Therefore, for 0.5 μm beads, a preferred dose is approximately $4\times10^9$ beads, for 0.05 μm beads, a preferred dose is approximately $4\times10^{12}$ beads, for 3 μm beads, a preferred dose is $2\times10^7$ beads. However, any dose that is effective in treating the particular condition to be treated is encompassed by the current invention.

In certain embodiments, the subject composition or subject pharmaceutical composition containing the subject microparticles or nanoparticles (e.g., carboxylated particles) induces immune tolerance when administered to the subject in need thereof.

In a further embodiment, the subject composition or subject pharmaceutical composition containing the subject microparticles or nanoparticles (e.g., carboxylated particles) ameliorates an inflammatory immune response when administered to the subject in need thereof.

Efficacy Tests

The effectiveness of the subject microparticles and nanoparticles against the treatable diseases and conditions can be tested using a number of efficacy tests, including suitable animal models.

A proxy for tolerogenic activity is the ability of a particle to stimulate the production of an appropriate cytokine at the target site. The immunoregulatory cytokine released by T suppressor cells at the target site is thought to be TGF-β (Miller et al., *Proc. Natl. Acad. Sci. USA*, 89:421, 1992). Other factors that may be produced during tolerance are the cytokines IL-4 and IL-10, and the mediator PGE. In contrast, lymphocytes in tissues undergoing active immune destruction secrete cytokines such as IL-1, IL-2, IL-6, and IFNγ. Hence, the efficacy of a subject particle can be evaluated by measuring its ability to stimulate the appropriate type of cytokines.

For example, a rapid screening test for a subject particle, effective mucosal binding components, effective combinations, or effective modes and schedules of mucosal administration can be conducted using animal model systems. Animals are treated at a mucosal surface with the test particle composition, and at some time are challenged with administration of the disease causing antigen or an infectious agent. Spleen cells are isolated, and cultured in vitro in the presence of the disease causing antigen or an antigen derived from the infectious agent at a concentration of about 50 μg/mL. Cytokine secretion into the medium can be quantified by standard immunoassay.

The ability of the subject particles to suppress the activity of cells can be determined using cells isolated from an animal immunized with the modified particles, or by creating a cell line responsive to a disease causing antigen or viral antigen target antigen (Ben-Nun et al., *Eur. J. Immunol.*, 11195, 1981). In one variation of this experiment, the suppressor cell population is mildly irradiated (about 1000 to 1250 rads) to prevent proliferation, the suppressors are co-cultured with the responder cells, and then tritiated thymidine incorporation (or MTT) is used to quantitate the proliferative activity of the responders. In another variation, the suppressor cell population and the responder cell population are cultured in the upper and lower levels of a dual chamber transwell culture system (Costar, Cambridge Mass.), which permits the populations to co-incubate within 1 mm of each other, separated by a polycarbonate membrane (WO 93/16724). In this approach, irradiation of the suppressor cell population is unnecessary, since the proliferative activity of the responders can be measured separately.

The effectiveness of compositions and modes of administration for treatment of specific disease can also be elaborated in a corresponding animal disease model. The ability of the treatment to diminish or delay the symptomatology of the disease is monitored at the level of circulating biochemical and immunological hallmarks of the disease, immunohistology of the affected tissue, and gross clinical features as appropriate for the model being employed. Non-limiting examples of animal models that can be used for testing are included below.

For example, animal models for the study of autoimmune disease are known in the art. Animal models which appear most similar to human autoimmune disease include animal strains which spontaneously develop a high incidence of the particular disease. Examples of such models include, but are not limited to, the non-obese diabetic (NOD) mouse, which develops a disease similar to type 1 diabetes, and lupus-like disease prone animals, such as New Zealand hybrid, MRL-Faslpr and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-1 receptor antagonist knockout for rheumatoid arthritis.

The invention contemplates modulation of tolerance by modulating TH1 response, TH2 response, TH17 response, or a combination of these responses. Modulating TH1 response encompasses changing expression of, e.g., interferon-gamma. Modulating TH2 response encompasses changing expression of, e.g., any combination of IL-4, IL-5, IL-10, and IL-13. Typically, an increase (decrease) in TH2 response will comprise an increase (decrease) in expression of at least one of IL-4, IL-5, IL-10, or IL-13; more typically an increase (decrease) in TH2 response will comprise an increase in expression of at least two of IL-4, IL-5, IL-10, or IL-13, most typically an increase (decrease) in TH2 response will comprise an increase in at least three of IL-4, IL-5, IL-10, or IL-13, while ideally an increase (decrease) in TH2 response will comprise an increase (decrease) in expression of all of IL-4, IL-5, IL-10, and IL-13. Modulating TH17 encompasses changing expression of, e.g., TGF-beta, IL-6, IL-21 and IL-23, and effects levels of IL-17, IL-21 and IL-22.

Tolerance to autoantigens and autoimmune disease is achieved by a variety of mechanisms including negative selection of self-reactive T cells in the thymus and mechanisms of peripheral tolerance for those autoreactive T cells that escape thymic deletion and are found in the periphery. Examples of mechanisms that provide peripheral T cell tolerance include "ignorance" of self antigens, anergy or unresponsiveness to autoantigen, cytokine immune deviation, and activation-induced cell death of self-reactive T cells. In addition, regulatory T cells have been shown to be involved in mediating peripheral tolerance. See, for example, Walker et al. (2002) *Nat. Rev. Immunol.*, 2:11-19; Shevach et al. (2001) *Immunol. Rev.*, 182:58-67. In some situations, peripheral tolerance to an autoantigen is lost (or broken) and an autoimmune response ensues. For example, in an animal model for EAE, activation of antigen presenting cells (APCs) through TLR innate immune receptors was shown to break self-tolerance and result in the induction of EAE (Waldner et al. (2004) 1 *Clin. Invest.*, 113:990-997).

Accordingly, in some embodiments, the invention provides methods for increasing antigen presentation while suppressing or reducing TLR7/8, TLR9, and/or TLR 7/8/9 dependent cell stimulation. As described herein, administration of particular subject particles results in antigen presentation by DCs or APCs while suppressing the TLR 7/8, TLR9, and/or TLR7/8/9 dependent cell responses associated with immunostimulatory polynucleotides. Such suppression may include decreased levels of one or more TLR-associated cytokines.

The subject invention also provides novel compounds that have biological properties useful for the treatment of Mac-1 and LFA-1 mediated disorders.

Pharmaceutical Composition

One aspect of the present invention provides pharmaceutical compositions which comprise the subject microparticles and nanoparticles, and optionally comprise a pharmaceutically acceptable carrier. In certain embodiments, these compositions optionally further comprise one or more additional therapeutic agents. Alternatively, the subject particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, or it may be any one of a number of agents undergoing approval in the Food and Drug Administration that ultimately obtain approval for the treatment of any disorder characterized by an uncontrolled inflammatory immune response or a bacterial or viral infection. It will also be appreciated that certain of the subject particles of present invention can exist in free form for treatment, or where appropriate, as a pharmaceutically acceptable derivative thereof.

In certain embodiments, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility.

The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The microparticles and nanoparticles can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

The present invention encompasses pharmaceutically acceptable topical formulations of the carboxylated microparticles and nanoparticles. The term "pharmaceutically acceptable topical formulation," as used herein, means any formulation which is pharmaceutically acceptable for intradermal administration of the subject microparticles/ nanoparticles by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, *Remington's Pharmaceutical Sciences,* 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations.

Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the modified particles. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least the carboxylated microparticles and nanoparticles and a penetration enhancing agent. The choice of topical formulation will depend on several factors, including the condition to be treated, the physicochemical characteristics of the particles and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, 111 (1997). In certain exemplary embodiments, penetration agents for use with the invention include, but are not limited to, triglycerides (e.g., soybean oil), aloe compositions (e.g., aloe vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

The carboxylated microparticles and nanoparticles can be administered by aerosol. This is accomplished by preparing an aqueous aerosol, liposomal preparation or solid particles containing the modified particles. A non aqueous (e.g., fluorocarbon propellant) suspension could be used.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It will also be appreciated that the carboxylated nanoparticles and microparticles and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

In certain embodiments, the pharmaceutical compositions containing the carboxylated particles of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, anti nausea medications and anti-sickness drugs.

The following examples are given to illustrate the present invention. It should be understood, however, that the invention is not to be limited to the specific conditions or details described in these examples. Throughout the specification, any and all references to a publicly available document, including any U.S. patent or patent application publication, are specifically incorporated by reference.

EXAMPLES

Example 1. Preparation of Carboxylated PLGA Nanoparticles Via Emulsification Process with Hyaluronic Acid 0.75 g PLGA (Lakeshore DLG 5050 4.5 A) was dissolved in 15 ml methylene chloride. The PLGA solution was mixed with 150 ml 1% polyvinyl alcohol solution containing 0.2 gram of hyaluronic acid, and homogenized at 12,500 rpm for 90 seconds on a NISSEN Homogenizer. The resulting emulsion was poured to a glass container and stirred magnetically at 400 rpm for 4 hours to allow the evaporation of the solvent. The nanoparticles were washed three times with distilled water before they were lyophilized.

Particle size and zeta potential were determined with a Malvern particle size analyzer (Worcestershire, UK). The average particle size was found to be 122.5 nm and zeta potential was −31.2 mV.

Example 2. Preparation of Carboxylated PLGA Nanoparticles Via Emulsification Process with a Short-Chain PLGA Polymer 0.19 g PLGA (Lactel B6013, inherent viscosity 0.15-0.25 dL/g) was dissolved in 10 ml methylene chloride. The PLGA solution was mixed with 100 ml 1% polyvinyl alcohol solution and homogenized at 18,400 rpm for 45 seconds with an IKA T25_digital_ULTRA-TURRAX Homogenizer. The resulting emulsion was poured to a glass container and stirred magnetically at 400 rpm for 4 hours to allow the evaporation of the solvent. The nanoparticles were washed three times with distilled water before they were lyophilized.

Particle size and zeta potential were determined with a Beckman-Coulter LS320 Laser Diffraction Particle Size Analyzer. The average particle size was found to be 680 nm.

Example 3. Preparation of Carboxylated PLGA Nanoparticles Via Precipitation Process with a Short-Chain PLGA Polymer 0.42 g PLGA polymer (Lakeshore DLG 5050 1A, inherent viscosity 0.05-0.15 dL/g) was dissolved in 10 ml acetone. This PLGA/acetone solution was added using a syringe pump at an addition rate of about 25 mL/hour to 60 mL 1 mM NaOH solution. The resulting nanoparticle suspension was mixed with 1 liter of distilled water and concentrated to approximately 20 mL with a tangential flow filtration device and a 500 kDa molecular weight cut-off module. The concentrated nanoparticle suspension was lyophilized.

Particle size and zeta potential were determined with a Malvern particle size analyzer (Worcestershire, UK). The average particle size was found to be 230.4 nm and zeta potential was −31.1 mV.

Example 4. Preparation of Carboxylated PLGA Nanoparticles Via Emulsification Process with a Short-Chain PLGA Polymer Containing Two Terminal Carboxyl Groups 0.22 g PLGA (Lactel B6013, initiated by glycolic acid) containing terminal COOH groups on both chain ends was dissolved in 10 ml methylene chloride. The PLGA solution was mixed with 150 ml 1% polyvinyl alcohol in 1 mM NaOH solution and homogenized at 18,000 rpm for 60 seconds on a NISSEN Homogenizer. The resulting emulsion was poured to a glass container and stirred magnetically at 500 rpm for 4 hours to allow the evaporation of the solvent. The nanoparticles were washed three times with distilled water before lyophilization.

Example 5. Preparation of Carboxylated PLGA Nanoparticles Via Emulsification Process with Hyaluronic Acid 0.75 g PLGA (Lakeshore DLG 5050 4.5A) is dissolved in 15 ml ethyl acetate to form a PLGA solution. The PLGA solution is then mixed with a mixture consisting essentially of 138.75 ml 1% polyvinyl alcohol solution (in water), 11.25 ml of ethyl acetate, and 0.2 gram of hyaluronic acid, and is homogenized at 12,500 rpm for 90 seconds on a NISSEN Homogenizer. The resulting emulsion is poured to a glass container and stirred magnetically at 400 rpm for 4 hours to allow the evaporation of the solvent. The nanoparticles are washed three times with distilled water before they are lyophilized.

The invention claimed is:

1. A method for preparing PLGA microparticles or nanoparticles having negative surface charges, said method comprising:
   (1) dissolving an active pharmaceutical ingredient (API) in an inner aqueous solvent to form an API solution;
   (2) dissolving a pharmaceutically acceptable PLGA polymer having an average molecular weight of from about 1,000 to about 1,000,000 Da, in an organic solvent to form a polymer solution, wherein the organic solvent is not miscible or is partially miscible in the inner aqueous solvent;
   (3) emulsifying the API solution in the PLGA polymer solution;
   (4) dissolving a pharmaceutically acceptable polyacrylic acid and polyvinyl alcohol to form an outer aqueous solution;
   (5) emulsifying the solution of step (3) in the outer aqueous solution to form an emulsion; and
   (6) removing the organic solvent to form said PLGA microparticles or nanoparticles having negative surface charges;
   wherein the microparticles or nanoparticles have a zeta potential of from about −15 mV to −100 mV and wherein the pharmaceutically acceptable polyacrylic acid is incorporated onto and at least partially into the PLGA microparticles.

2. The method of claim 1, wherein the organic solvent is selected from the group consisting of methylene chloride, ethyl acetate, or chloroform, and mixtures thereof.

3. The method of claim 1, wherein each emulsifying step comprises homogenization.

4. The method of claim 1, wherein the organic solvent is removed through evaporation.

5. The method of claim 1, wherein the pH of the outer aqueous solution is between about 6 to about 10.

6. The method of claim 1, wherein the microparticles or nanoparticles have average particle sizes of from about 10 nm to about 100 μm.

7. The method of claim 1, wherein the microparticles or nanoparticles have a zeta potential of from −35 mV to −85 mV.

8. A method for preparing PLGA microparticles or nanoparticles having negative surface charges, said method comprising:
   (1) dissolving an active pharmaceutical ingredient (API) in an inner aqueous solvent to form an API solution;
   (2) dissolving a pharmaceutically acceptable PLGA polymer having an average molecular weight of from about 1,000 to about 1,000,000 Da, in an organic solvent to form a polymer solution, wherein the organic solvent is not miscible or is partially miscible in the inner aqueous solvent;
   (3) emulsifying the API solution in the PLGA polymer solution;
   (4) dissolving a pharmaceutically acceptable negatively charged polymer and polyvinyl alcohol to form an outer aqueous solution;
   (5) emulsifying the solution of step (3) in the outer aqueous solution to form an emulsion; and
   (6) removing the organic solvent to form said PLGA microparticles or nanoparticles having negative surface charges;

wherein the microparticles or nanoparticles have a zeta potential of from about −15 mV to −100 mV and wherein the pharmaceutically acceptable negatively charged polymer is incorporated onto and at least partially into the PLGA microparticles.

9. The method of claim 8, wherein the organic solvent is selected from the group consisting of methylene chloride, ethyl acetate, or chloroform, and mixtures thereof.

10. The method of claim 8, wherein each emulsifying step comprises homogenization.

11. The method of claim 8, wherein the organic solvent is removed through evaporation.

12. The method of claim 8, wherein the pH of the outer aqueous solution is between about 6 to about 10.

13. The method of claim 8, wherein the microparticles or nanoparticles have average particle sizes of from about 10 nm to about 100 µm.

14. The method of claim 8, wherein the microparticles or nanoparticles have a zeta potential of from −35 mV to −85 mV.

15. The method of claim 8, wherein the pharmaceutically acceptable negatively charged polymer is poly(ethylene-alt-maleic acid) (PEMA).

\* \* \* \* \*